United States Patent [19]
Bedi et al.

[11] Patent Number: 4,586,502
[45] Date of Patent: May 6, 1986

[54] SURGICAL INSTRUMENT ACTUATOR WITH NON-COLLINEAR HYDRAULIC PISTONS

[75] Inventors: James J. Bedi, Stockton; Donald M. Golden, Cherry Hill; James A. Transue, Somerville, all of N.J.

[73] Assignee: Ethicon, Inc., Somerville, N.J.

[21] Appl. No.: 636,477

[22] Filed: Jul. 31, 1984

Related U.S. Application Data

[63] Continuation-in-part of Ser. No. 345,438, Feb. 3, 1982, abandoned.

[51] Int. Cl.$^4$ .................. A61B 17/00; A61B 17/12
[52] U.S. Cl. ................................................ 128/334 R
[58] Field of Search .............. 128/334 R, 303 R, 325, 128/326; 227/DIG. 1 A, DIG. 1 C; 604/61-64, 223; 29/243.5, 243.56; 254/93; 177/208

[56] References Cited

U.S. PATENT DOCUMENTS

| | | | |
|---|---|---|---|
| 1,945,377 | 1/1934 | Posnack | 227/DIG. 1 |
| 2,767,400 | 10/1956 | Haberstump | 227/DIG. 1 |
| 2,883,984 | 4/1959 | Candido | 604/61 |
| 3,402,712 | 9/1968 | Eisenhand | 604/61 |
| 3,638,652 | 2/1972 | Kelly | 128/334 R |
| 3,653,117 | 4/1972 | Wolfberg | 227/DIG. 1 |
| 3,952,747 | 4/1976 | Kimmell | 128/303 R |
| 4,049,177 | 9/1977 | Bussard | 227/DIG. 1 |
| 4,129,955 | 12/1978 | Schommer | 604/223 |
| 4,331,277 | 5/1982 | Green | 227/DIG. 1 |
| 4,349,028 | 9/1982 | Green | 227/DIG. 1 |

Primary Examiner—Lucille M. Phynes
Attorney, Agent, or Firm—Robert L. Minier

[57] ABSTRACT

A hand-operated surgical instrument for implanting a fastener in tissue to close a movable operating member remote from or extending from a movable handle for actuating the operating member. A hydraulic actuating means comprising first and second connected chambers oriented at angles relative to one another effect the movement of the operating member when the handle is moved relative to the instruments.

2 Claims, 15 Drawing Figures

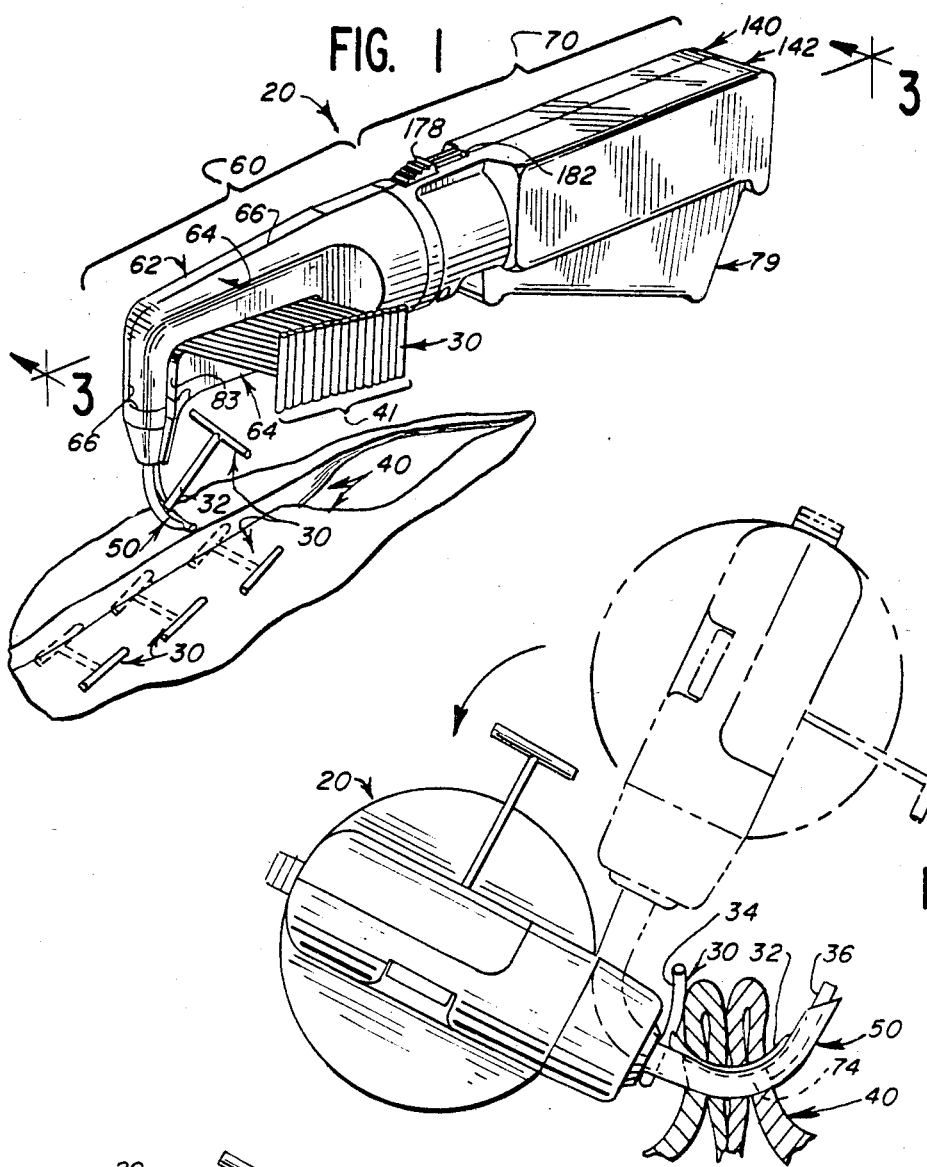
FIG. 1
FIG. 2a
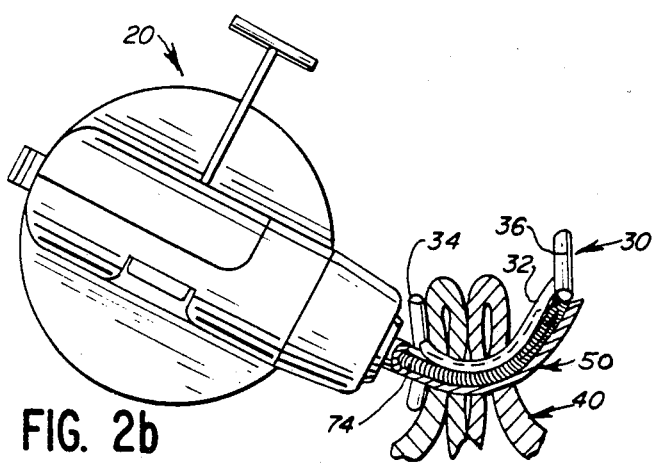
FIG. 2b
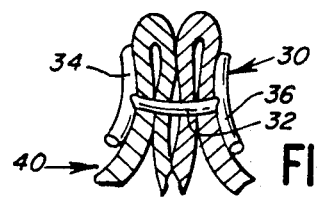
FIG. 2c

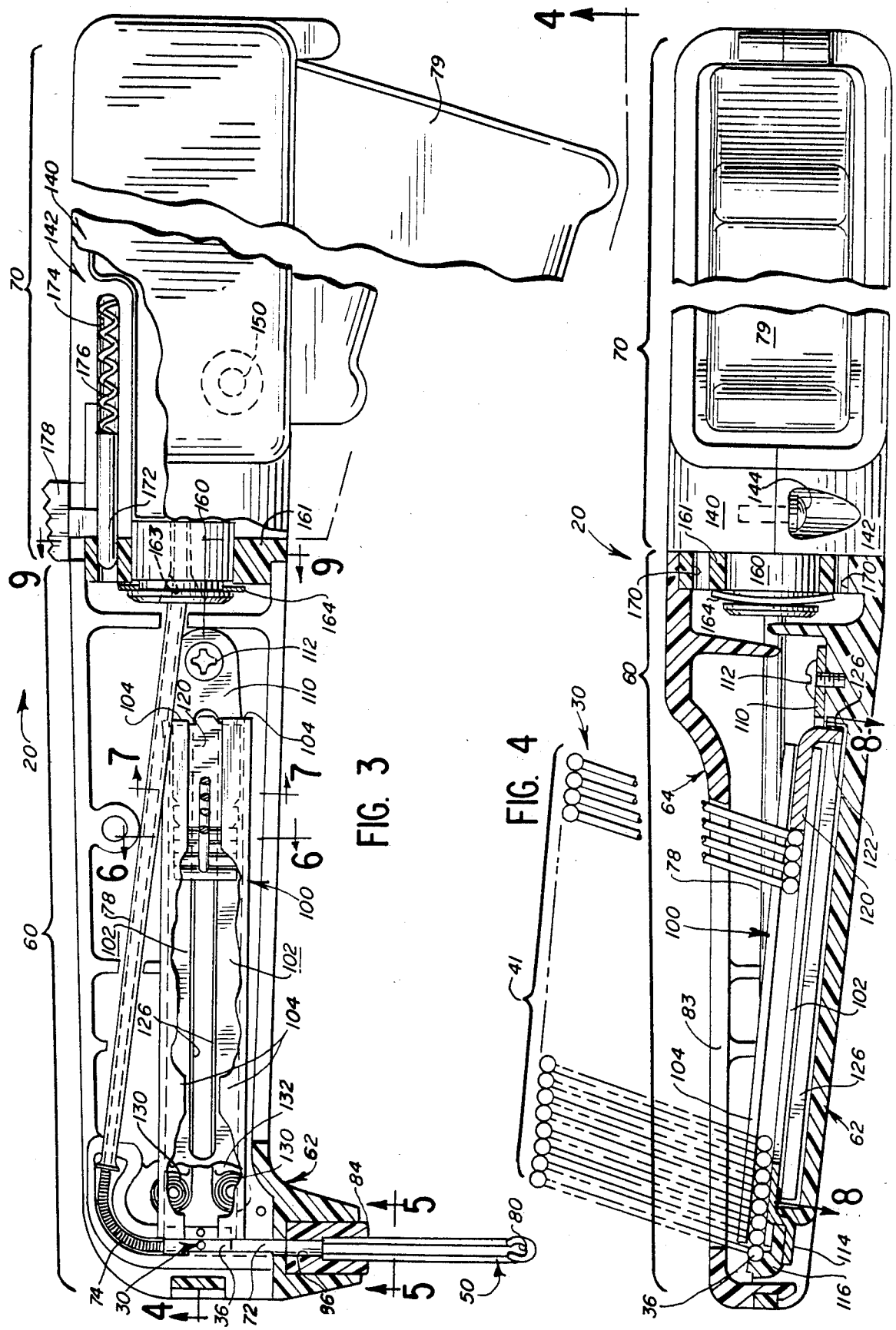

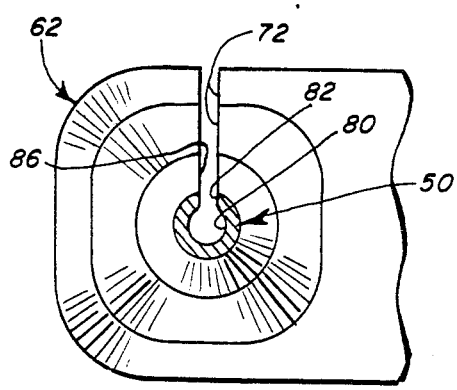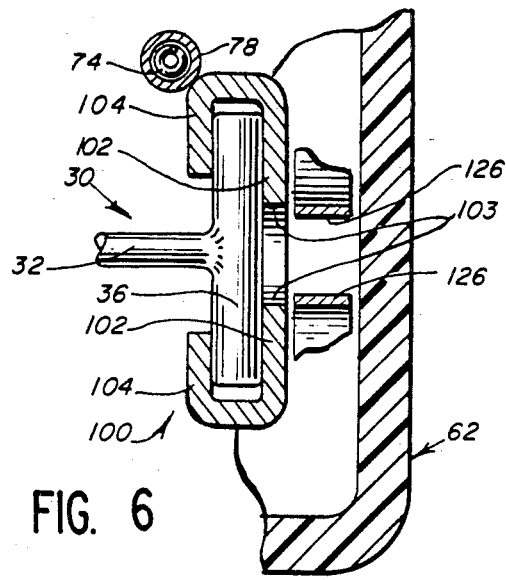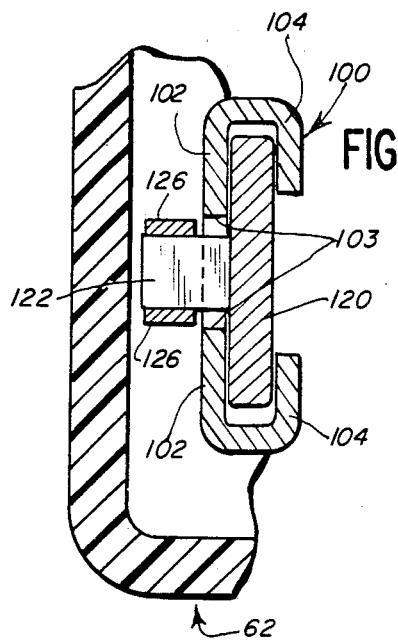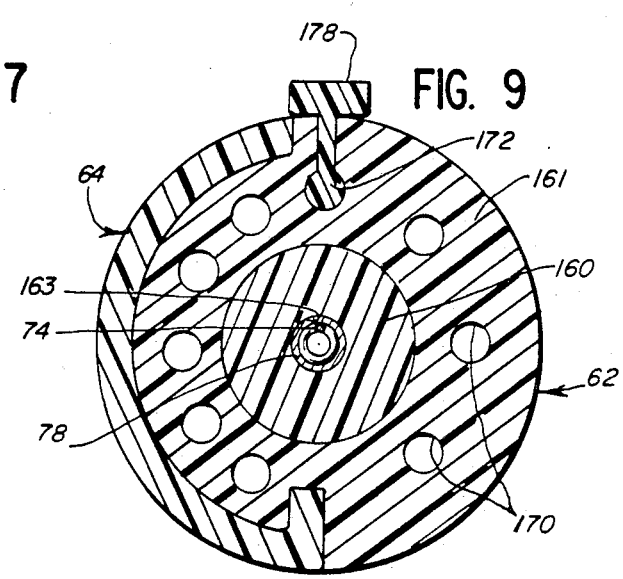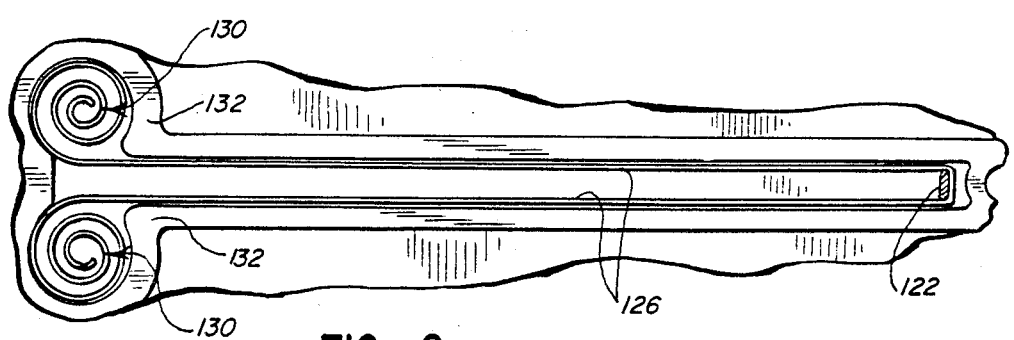

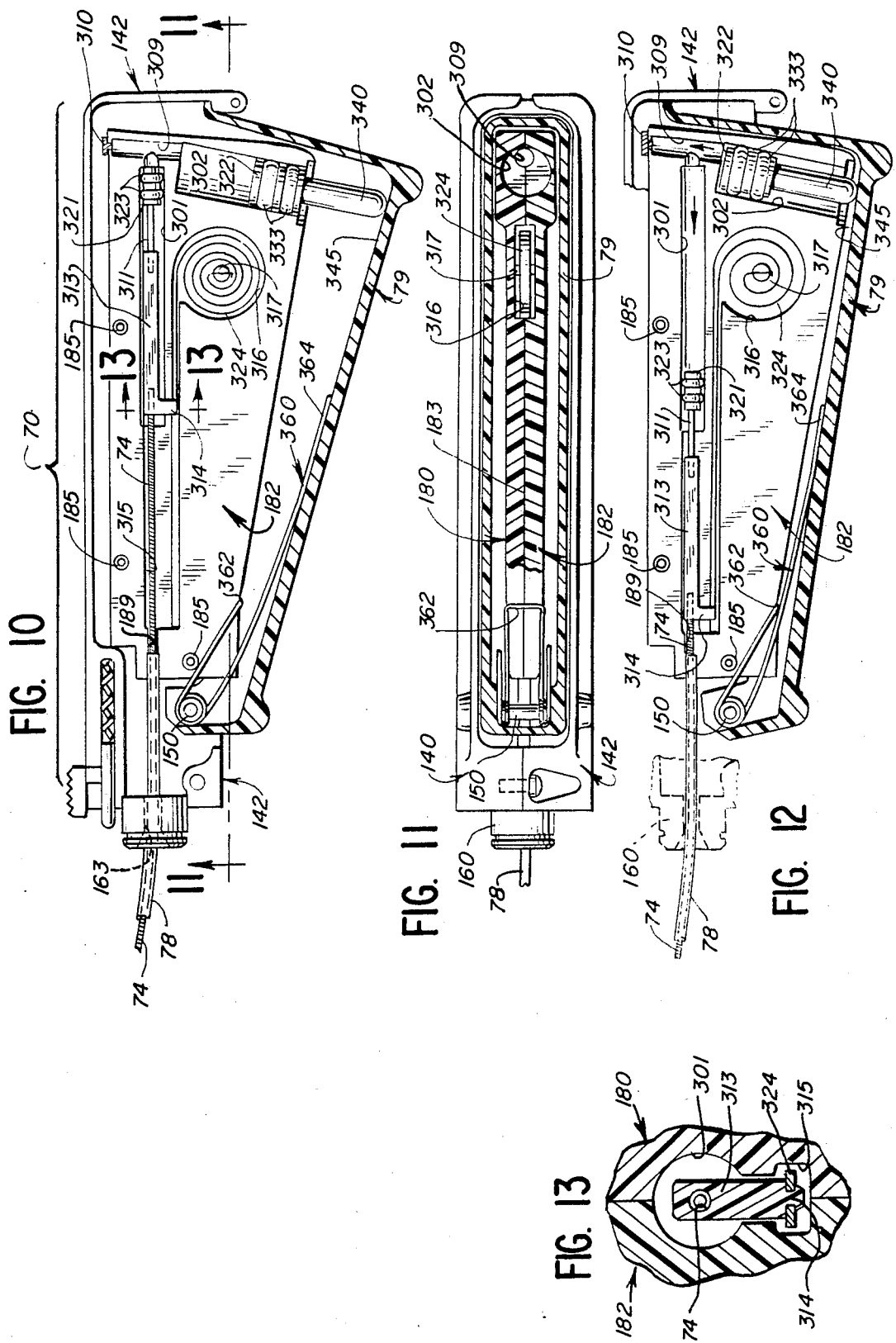

SURGICAL INSTRUMENT ACTUATOR WITH NON-COLLINEAR HYDRAULIC PISTONS

RELATED APPLICATIONS

This is a continuation-in-part application of copending patent application Ser. No. 345,438, filed Feb. 3, 1982, now abandoned.

TECHNICAL FIELD

This invention relates to hand-operated surgical instruments, and more particularly to a mechanism for transmitting a force applied by hand at the instrument handle to a movable operating member that is remote from the handle.

BACKGROUND OF THE INVENTION

A variety of hand-held surgical instruments have been proposed and/or are in use today for effecting a variety of surgical procedures or other operations that are performed upon human or animal anatomical structures, such as bone and tissue, including skin, muscle, and fascia. Some of these instruments are also used to effect certain operations with, or on, foreign bodies or prosthetic devices that may be implanted in, or carried by, a human or animal subject. Examples of the above-described instruments include instruments for applying ligating clips to blood vessels, bone crushing instruments, pin cutting instruments, instruments for applying staples or other types of fasteners to tissue, and the like.

Many of these types of instruments are held in one hand by the surgeon and include one or more movable operating elements or members (e.g., crimping or gripping jaws) which are located toward an end of the instrument that is spaced from, or remote from, the surgeon's hand. Typically, such an instrument includes an operating handle mechanism, which may be a reciprocative element, a single lever, a pair of scissors-type levers, or other suitable mechanism. The operating member or members are connected through mechanical linkages to the handle mechanism. Manipulation of the handle mechanism by the surgeon causes the desired movement of the operating member or members so as to effect the desired operation, such as applying a ligating clip to a blood vessel, cutting a pin, crushing a bone, inserting a staple or fastener into tissue, and the like.

A method has been proposed for using an instrument or device for closing wounds or surgical incisions in mammalian tissue with fasteners made from flexible and resilient biocompatible material which may be either absorbable or nonabsorbable in body tissue. One such type of device for applying such a fastener to tissue is generally disclosed in U.S. Pat. No. 4,006,747.

The device disclosed in U.S. Pat. No. 4,006,747 generally includes a slotted hollow needle in which is carried a portion of the fastener, a rigid plunger for pushing the fastener along the needle and into the tissue, and a mechanism for moving the plunger into the needle and then for withdrawing the plunger from the needle.

Other devices of the type disclosed in U.S. Pat. No. 4,006,747 suitable for use in applying various types of fasteners are disclosed in U.S. Pat. Nos. 3,470,834, 3,103,666, 2,069,878, 3,494,004, 3,399,432, 3,518,729, and U.S. Pat. No. Des. 313,418.

Other devices for applying fasteners in a non-surgical situation are disclosed in U.S. Pat. Nos. 3,209,422 and 3,733,657.

Prior to the disclosure in U.S. Pat. No. 4,006,747 of the method for applying a fastener simultaneously through a needle and tissue, procedures for the manual application of sutures or fasteners through tissue with needles or needle-like elements were known. Examples of such sutures and needles are disclosed in U.S. Pat. Nos. 3,636,956, and 3,716,058.

In none of the above-discussed procedures or devices is a hydraulic actuating mechanism used to effect the desired operation, such as placing a fastener through tissue. The inventors of the present invention have determined that it would be desirable to provide a type of hydraulic actuating mechanism for use in a wide variety of surgical instruments, including in the fastener applying devices described above.

Further, it would be beneficial to provide such a hydraulic mechanism that could either amplify the movement of the instrument operating member relative to the handle movement or amplify the force of the operating member relative to the force applied at the handle. In addition, it would be desirable to provide such a hydraulic actuating mechanism with means for automatically returning the instrument handle to an unactuated or released position.

Also, it would be advantageous if instruments of the class described could be provided with the hydraulic actuating mechanism of the type described wherein the hydraulic actuating mechanism was relatively small and compact so as to permit incorporation of the mechanism in a housing that could be easily grasped and manipulated with one hand by the surgeon.

With such a hydraulic mechanism, the inventors have found that it would be desirable to arrange the hydraulic cylinder and piston components within the housing so as to be operably engaged with the handle through a minimum of mechanical connections or linkages.

It would be also beneficial if the hydraulic actuating mechanism could be made from relatively inexpensive materials, along with the other instrument components, so that the instrument, after being initially provided to the surgeon in a sterile package, can be disposed of after one use. With such a disposable instrument, it would be desirable to provide a hydraulic actuating mechanism that could be fabricated, along with the other components of the instrument, from non-toxic materials that would have little or no deleterious effects on the environment as a result of proper disposal of the instrument after use.

SUMMARY OF THE INVENTION

The present invention provides a novel hydraulic actuating mechanism for surgical instruments. In a preferred form disclosed herein, the present invention contemplates a novel actuating mechanism for, and other modifications to, the fastener applying device of the general type disclosed in U.S. Pat. No. 4,006,747.

In general, the novel actuating system can be used in those hand-operated surgical instruments that have at least one movable operating member remote from or extending from a movable handle means for actuating the operating member. The system includes a hydraulic actuating mechanism operably connected between the handle means and the operating member for effecting the movement of the operating member when the handle means is moved relative to the instrument. The system further includes a biasing means for returning the operating member and the handle means to their unactuated positions.

In a preferred form of the invention, the actuating system is incorporated in a fastener applying device that is adapted for closing a wound or incision in tissue with a fastener. The fastener is of the type comprising a filament member terminated at one end by a first anchoring means and at the other end by a second anchoring means. The fastener is applied by the device to remain in the tissue with the filament member transversing the wound or incision through the tissue and with the first and second anchoring means maintaining the tissue in approximation at the wound or incision from points on the surface of the tissue on either side of the wound or incision.

Preferably, the device includes a housing in which, inter alia, the actuating system is disposed. A hollow needle extends outwardly from the housing and has a distal end adapted for piercing the tissue. The needle defines a passage therein for receiving the first anchoring means of the fastener. The passage in the needle extends along the length of the needle from an entrance aperture to a discharge aperture at the distal end of the needle. The needle also defines a slot communicating with the passage along the length of the needle from the entrance aperature to the discharge aperture. The slot is adapted to receive a portion of the filament member.

The device also includes an operating member in the form of an elongate pusher member adapted to reciprocate in the needle passage and adapted to engage the first anchoring means of the fastener for pushing the fastener along the needle.

The actuating means includes first and second connected chambers in the housing. Each chamber has a generally cylindrical configuration and the second chamber is oriented with its longitudinal axis at an angle relative to the longitudinal axis of the first chamber so as to provide a compact arrangement that eliminates the need for an undesirably long housing. First and second pistons are slidably disposed in the first and second chambers, respectively. A substantially incompressible fluid occupies the volume within the connected first and second chambers between the first and second pistons.

The first piston is connected with the elongate pusher member. The device includes a camming means associated with the handle means and a cam follower means connected with the second piston for engaging the camming means and being moved by the handle means to force the second piston along the second chamber. Movement of the second piston forces the fluid from the second chamber into the first chamber to move the first piston from a first position to a second position to effect the desired movement of the connected pusher member.

The length of the pusher member and the stroke of the first piston is selected so that the pusher member can be reciprocated between (1) a retracted position spaced inwardly from the discharge aperture of the needle and (2) an extended position outwardly along the needle relative to the retracted position wherein the fastener is ejected from the discharge aperture of the needle by the pusher member.

Preferably, a constant force biasing means is also provided for biasing the first piston from the second position to the first position to cause the pusher member to be returned to the retracted position after a fastener has been applied with the device.

Preferably, in the preferred form of the present invention, the operating stroke of the first piston is longer than the operating stroke of the second piston. Therefore, the movement of the connected pusher member is amplified relative to the movement of the second piston and handle means.

The present invention resides in the combination, construction, arrangement, and disposition of various component parts and elements incorporated in the device in accordance with the principles of this invention. The present invention will be better understood and important features others than those specifically enumerated above will become apparent when consideration is given to the following details and description which, when taken in conjunction with the annexed drawings, describes, discloses, illustrates, and shows a preferred embodiment of the present invention and what is present considered and believed to be the best mode of practicing the principles of the invention. Other embodiments and modifications may be suggested to those having the benefit of the teachings herein, and such other embodiments and modifications are intended to be reserved, especially as they fall within the scope and spirit of the subjoined claims.

BRIEF DESCRIPTION OF THE DRAWINGS

In the accompanying drawings forming part of the specification, and in which like numerals are employed to designate like parts throughout the same, FIG. 1 is a perspective view of a first embodiment of a hand-held surgical fastener applier instrument of the present invention shown being used to close an incision in tissue in a surgical procedure;

FIG. 2a is an end view of the fastener applier instrument of FIG. 1 and a fragmentary, partial cross-sectional view of the tissue with the instrument shown in dashed line in a first position as the needle pierces the tissue and with the instrument shown in solid line in a moved position while placing a fastener across the incision;

FIG. 2b is a view similar to FIG. 2a but showing a stage in the surgical procedure that is later than that illustrated in FIG. 2a and showing the needle in partial cross-section;

FIG. 2c is a fragmentary, cross-sectional view of the tissue after the fastener applier instrument has been removed so as to leave the fastener in place across the incision;

FIG. 3 is an enlarged, partial cross-sectional view taken generally along the plane 3—3 in FIG. 1 but modified to show the instrument in the unactuated or released mode;

FIG. 4 is a partial cross-sectional view taken generally along the planes 4—4 in FIG. 3;

FIG. 5 is a cross-sectional view taken generally along the plane 5—5 in FIG. 3;

FIG. 6 is a fragmentary, enlarged, cross-sectional view taken generally along the plane 6—6 in FIG. 3;

FIG. 7 is a fragmentary, enlarged, cross-sectional view taken generally along the plane 7—7 in FIG. 3;

FIG. 8 is a fragmentary, enlarged, cross-sectional view taken generally along the plane 8—8 in FIG. 4;

FIG. 9 is an enlarged, cross-sectional view taken generally along the plane 9—9 in FIG. 3;

FIG. 10 is a fragmentary, cross-sectional view similar to FIG. 3 but showing only the rear portion of the fastener applier instrument of the present invention, which rear portion contains the handle means and actuating means shown in the unactuated or released position;

FIG. 11 is a fragmentary, cross-sectional view taken generally along the plane 11—11 in FIG. 10;

FIG. 12 is a view similar to FIG. 10 but with some of the housing structure eliminated for convenience of illustration and showing the handle means and actuating means in the moved or actuated position; and FIG. 13 is a fragmentary, cross-sectional view taken generally along the plane 13—13 in FIG. 10.

DESCRIPTION OF THE PREFERRED EMBODIMENT

This invention may be used in many different forms. This specification and the accompanying drawings disclose only one specific form as an example of the use of the invention. The invention is not intended to be limited to the embodiment illustrated, and the scope of the invention will be pointed out in the appended claims.

The precise shapes and sizes of the components herein described are not essential to the invention unless otherwise indicated.

For ease of description, the device of this invention will be described in an orientation as illustrated in the figures and terms such as upper, lower, horizontal, etc., will be used with reference to this orientation. It will be understood, however, that the device of this invention may be manufactured, stored, transported, used, and sold in an orientation other than the position described.

In the following description, reference is made to the industry standards of the American Iron and Steel Institute, 1000 16th Street, N.W., Washington, D.C. U.S.A. 20036. These standards will be designated by the common initial letters "AISI" followed by a suffix comprising additional alphanumeric characters and the standards are understood to be those in effect as of Aug. 1, 1981.

For ease of understanding the present invention, the invention is illustrated in a preferred embodiment comprising a hand-held, hand-operated device for closing a wound or incision in tissue with a particular type of fastener. Before describing in detail the various components of the fastener applier device, the fastener and the general method of applying the fastener with the device will first be described. This will be followed by a detailed description of the elements comprising the fastener applying device.

THE FASTENER

FIG. 1 illustrates a method of applying, with a fastener applier device 20 of the present invention, a plurality of fasteners 30 to skin or other tissue 40 in a surgical procedure.

The fastener 30 is identical to the flexible fastener disclosed in the U.S. Pat. No. 4,006,747 and reference is directed thereto for a complete description of such a fastener. Briefly, with reference to FIG. 2c of the drawings annexed hereto, the fastener 30 includes a filament member 32 terminated at one end by first anchoring means or rod-shaped head 36 and at the other end by an identical second anchoring means or rod-shaped head 34.

The fastener 30 is conveniently H-shaped and constructed of a flexible and resilient biocompatible material which may be either absorbable or non-absorbable in body tissue. As disclosed in detail in the above-referenced U.S. Pat. No. 4,006,747, the fastener 30 may be constructed of any of the wide variety of materials or combinations of materials. For example, materials such as nylon and polypropylene can be used to mold nonabsorbable fasteners 30 with good results. Also, copolymers of glycolide and lactide can also be used with good results and have the additional advantage of being absorbable in tissue and thus are particularly well suited for internal use in applications where long-term maintenance of wound support is not required.

As best illustrated in FIG. 1, a series of fasteners 30 are typically placed in close proximity along the length of the wound or incision to effectively close the wound or incision and enable natural healing to proceed. Non-absorbable fasteners are removed from the tissue closures by snipping off one head and withdrawing the fastener with the opposite head.

METHOD OF APPLYING THE FASTENER

As best illustrated in FIG. 2c, and as more fully described in the above referenced U.S. Pat. No. 4,006,747, the fastener 30 is used to close a wound or incision by first folding over the tissue 40 on each side of the wound or incision and then approximating the folded over portions. Next, with the folded tissue held, as by grasping it with forceps, the flexible fastener 30 is temporarily bent or deformed and inserted through the skin on both the sides of the wound or incision. This can be effected with a fastener applying device, such as the device 20 illustrated in FIGS. 1–2b, in the general manner disclosed in the above-referenced U.S. Pat. No. 4,006,747.

Specifically, the device 20 is provided with means for holding a plurality of fasteners 30 in an aligned row 41 as best illustrated in FIG. 1. The device 20 includes a hollow needle 50 adapted for receiving one rod-shaped head of the fastener 30 as best illustrated in FIG. 1. The needle 50 also has a longitudinally extending slot through which the filament 32 of the fastener projects. The device 20 is adapted to feed one fastener 30 at a time into the hollow, slotted needle 50 and to push the fastener along the needle.

As best illustrated in FIG. 2a, the needle 50 is passed into the approximated and folded tissue 40 from a point on one side of the wound and on through the tissue until the tip of the needle 50 exits the tissue on the opposite side of the wound.

The path of the needle 50 through the tissue is not unlike that followed in conventional suturing. While closing a wound by conventional suturing, the needle and a length of attached suture are passed completely through the tissue. The hollow needle in the present case is inserted only far enough to penetrate through the tissue to form an open communication with both sides of the wound.

As best illustrated in FIGS. 2a and 2b, the applier device 20 includes a flexible pusher member 74 (visible in FIG. 2b) that is adapted to reciprocate within the curved, hollow needle 50 and to engage and push an end of the fastener's rod-shaped head 36 through the hollow needle until it is discharged from the tip of the needle 50 on the far side of the wound. Then the needle 50 is withdrawn from the tissue while the fastener 30 is restrained in the tissue 40 by the head 36 on the far side of the wound. The fastener is thus left in the tissue 40 with the filament 32 of the fastener 30 traversing the wound along the path created by the needle 50 and with the two anchoring means (the heads 34 and 36) engaging and restraining the surface of the tissue 40 on either side of the wound or incision.

Although the needle 50 is illustrated in FIGS. 1–2b as being curved and as guiding a flexible pusher member 74, it is to be realized that the device 20 of the present invention may have a substantially straight needle guiding a *rigid* pusher member as in the embodiment described and illustrated in the above-discussed U.S. Pat.

No. 4,006,747 and as disclosed in U.S. Pat. Nos. 3,470,834; 3,103,666; 2,069,878; 3,494,004; 3,394,432; 3,518,729; and U.S. Pat. No. Des. 313,418.

It has been found that when the needle 50 is curved and also projects downwardly and outwardly to one side of the fastener applier device 20 as illustrated in FIG. 1, certain advantages are realized. Specifically, the use of a needle having this type of orientation on the device 20 permits the surgeon to use a hand movement that is substantially similar to that used when applying conventional sutures with conventional suture needles. This is desirable since most surgeons have developed, and have become accustomed to, such hand movement when applying conventional sutures. Therefore, the adoption and use of the fastener applier device 20 of the present invention by a surgeon is more readily facilitated.

FIGS. 1–2c illustrate the tissue or skin 40 being folded over once at each side of the wound. It is to be realized that such a fold is not necessary when closing a wound or incision with the fastener 30 as installed by the fastener applier device 20 of the present invention. Specifically, reference is directed to FIGS. 2 and 4 of the above-discussed U.S. Pat. No. 4,006,747 for illustrations of the use of a fastener identical to the fastener 30 disclosed herein but wherein the tissue on each side of the wound is not folded over.

FASTENER APPLIER DEVICE MAGAZINE AND NEEDLE STRUCTURE

As best illustrated in FIG. 1, the device 20 has a generally elongate housing having a front or magazine portion 60 that contains the fastener row 41 and needle 50 and having a rear portion 70 that houses the actuating mechanism. A handle, trigger, or handle means 79 extends from the rear housing portion 70.

The first or front end portion 60 will next be described in detail with reference to FIGS. 1 and 3–5. With reference to FIG. 1, the front end portion 60 of the device preferably comprises two molded portions or pieces, piece 62 and piece 64. Each piece is preferably molded from a suitable material. For example, the pieces 62 and 64 may be molded from a polycarbonate resin such as that sold in the United States of America under the trademark or trade name Merlon M40 F by the Mobay Chemical Corporation.

Pieces 62 and 64 are mated together about a parting plane 66 (seen in FIG. 1 as the line running the length of the device 20). The pieces 62 and 64 are joined together by suitable means such as screws, adhesive, or other bonding means (not illustrated). In FIG. 3, the first piece 62 is viewed along its parting plane and is seen to define an arcuate channel 72 at the front end in which the flexible pusher member 74 is slidably disposed. The flexible pusher member 74 is preferably constructed from AISI 316 L Series stainless steel 30 gauge wire wound in a helical configuration having a radius slightly less than the radius of the arcuate channel 72.

The flexible pusher member 74 extends rearwardly in the device 20 from the front end of the housing magazine portion 60 through a hollow tube 78 into the rear portion 70 and is operatively engaged with the actuating means within the housing rear portion 70 as will be explained in detail hereinafter.

As best illustrated in FIGS. 1 and 4, the piece 64 of the housing front end portion 60 defines an L-shaped slot 83, the base leg portion of which L-shaped slot 83 is in registry with the arcuate channel 72 of the mating housing piece 62. The other leg of the L-shaped slot 83 receives the row 41 of fasteners 30.

The front end of the housing piece 62 has a generally conical configuration as best illustrated in FIGS. 1 and 5 and carries a needle holder insert 84 as best illustrated in FIG. 3. The needle holder insert 84 has a generally cylindrical configuration with a slot 86 in registry with the channel 72 of the housing piece 62.

The needle 50 is secured by a suitable means within the needle holder insert 84 and projects from the distal end thereof as best illustrated in FIGS. 3 and 5. The needle 50 is hollow and extends outwardly away from the housing piece 62. The distal end of the needle 50 is preferably angled or sharpened (as best illustrated in FIG. 2a) to facilitate the piercing of tissue.

The needle 50 defines a passage 80 as best illustrated in FIG. 5. The passage 80 extends along the length of the needle 50 from the entrance aperature of the needle within the needle holder insert 84 to the discharge aperture at the distal end of the needle 50. The needle 50 also defines a slot 82 along its length as best illustrated in FIG. 5. The slot 82 is coextensive with the passage 80 and therefore extends from the entrance aperture of the needle 50 within the needle holder insert 84 to the discharge aperture at the distal end of the needle 50. The slot 82 communicates with the passage 80 along the entire length of the needle 50. The passage 80 of the needle 50 is adapted to receive one of the fastener anchoring means or rod-shaped heads (head 36 in FIG. 2a). The slot 82 of the needle 50 is adapted to receive a portion of the filament 32 of the fastener 30.

In a preferred form of the invention illustrated, the needle 50 and the needle holder insert 84 are both preferably fabricated from a suitable metal, such as AISI 420 stainless steel. Preferably then the insert 84 and needle 50 are welded together to form an integral assembly which is then suitably secured within the conical portion of the housing piece 62.

As best illustrated in FIGS. 3 and 4, the front portion 60 of the fastener applier device 20 also includes a magazine 100 for holding a plurality of fasteners 30 in the row 41 and for feeding the fasteners 30 seriatim into the channel 72 defined in the front housing piece 62. Specifically, as best illustrated in FIGS. 3, 4, and 6, the magazine 100 includes a base member 102 defining a slot 103 and having a pair of angled retainer flanges 104 adapted to receive the fasteners 30. Specifically, the anchor means or rod-shaped head 36 of each fastener 30 is slidably received within the flanges 104 and on top of the slotted member 102. The fastener filament member 32 extends out of the magazine through the space defined between the flanges 104.

The magazine 100 is mounted within the housing portion 62 as best illustrated in FIGS. 3 and 4. Specifically, the rear end of the magazine 100 has a rearwardly extending tab 110 by which the magazine 100 is secured with a screw 112 to the housing portion 62. At the front end of the magazine 100, the magazine 100 has an off-set but forwardly extending tab 114 which is retained under a cross wall 116 of the housing portion 62.

Slidably disposed within the magazine 100 on top of the bottom member 102 is a feeder member 120 (FIGS. 4 and 7) which has a downwardly depending tab 122 disposed through the central slot 103 of the magazine bottom member 102.

The downwardly depending tab 122 of the feeder member 120 is biased forwardly with a band spring 126 as best illustrated in FIG. 4. As best illustrated in FIGS.

3, 7, and 8, the band spring has two oppositely coiled portions 130 which are disposed within a retainer or guide wall 132. The central portion of the band spring 126 is pulled outwardly from the coiled portions 130 and extends underneath and along the length of the magazine 100 to the feeder member tab 122 with which it is engaged. Thus, the feeder member 120 is continuously biased forwardly to push the fasteners 30 toward the channel 72 defined in the housing portion 62.

The guide tube 78, the arcuate channel 72 in the housing piece 62, and the channel 86 in the needle holder insert 84 all function as a guide means in the housing that serves to guide the movement of the flexible pusher member 74 into alignment with the entrance aperture and a passage 80 of the needle 50. Further, that portion of the channel 72 in the housing piece 62 immediately adjacent the front end of the magazine 100 can be regarded as defining a "fastener dispensing region" aligned with the entrance aperture of the needle 50 for accommodating admission of the fastener rod-shaped head 36 in registry or alignment with the entrance aperture and passage 80 (FIG. 5) of the needle 50.

As best illustrated in FIGS. 3 and 4, the width of the channel 72 in the housing portion 62 has a configuration and dimensions sufficient to accommodate the rod-shaped end of just one of the fasteners 30 at the front end of the magazine 100. The head 36 of the fastener is fed from the magazine 100 into the channel 72 just forward of the flexible pusher member 74 when the flexible pusher member 74 is in a fully retracted position. The channel 72 of the housing piece 62 thus serves to guide and align the flexible pusher member 74 and the rod-shaped head 36 of the fastener with the passage 80 of the needle 50. When the flexible member 74 is moved forwardly toward the needle 50 by suitable actuating means (described in detail hereinafter), the rod-shaped head 36 of the fastener 30 travels along the channel 72 of the housing portion 62, along the channel 86 of the needle holder insert 84, and finally through the needle 50. The flexible pusher member 74 is moved forwardly until its leading end pushes the fastener rod-shaped head 36 out of the needle passage 80 (as illustrated in detail in FIG. 2b).

After the rod-shaped head 36 of the fastener has been ejected from the needle discharge aperture, the flexible pusher member 74 is retracted back to the position illustrated in FIG. 3 (by means described in detail hereinafter). As long as the flexible pusher member 74 extends beyond the front of the magazine 100, the next fastener 30 in the magazine 100 is prevented from being fed from the magazine to the channel 72 in the housing piece 62. However, as soon as the flexible pusher member 74 has returned to a point just behind the magazine 100 as illustrated in FIG. 3, the next fastener 30 is urged forwardly into the channel 72 of the housing piece 62. Thus, the fastener applier device 20 is ready to apply the next fastener.

REAR HOUSING AND THE FRONT HOUSING ROTATION LATCH

As best illustrated in FIGS. 3 and 4, the rear housing portion 70, which contains the actuating means and the handle or trigger 79, is fabricated from two halves or pieces 140 and 142. In FIG. 3, a forward part of the rear housing piece 140 is broken away along the parting plane to show the other rear housing piece 142. As best illustrated in FIGS. 3 and 4, the housing pieces 140 and 142 are suitably secured together, as with screws, one of which screws 144 is visible in FIG. 4. These pieces 140 and 142 are preferably molded from the same materials as the housing front portion 60 described above.

Preferably the handle or trigger 79 is molded from the same material as the other housing pieces and is pivotably mounted to the rear housing portion 70 about a pivot shaft 150 as illustrated in FIGS. 3 and 10. To operate the trigger 79, the device 20 is typically grasped with the palm of the hand at the top of the rear housing 70 (as viewed in FIG. 3) with the fingers and/or thumb extending down to the trigger 79. The trigger 79 is operably connected with an actuating means, described hereinafter in detail, to move the flexible pusher member 74 from the retracted position (illustrated in FIG. 3) to the extended position (illustrated in FIG. 2b) wherein the fastener 30 is ejected from the discharge aperture of the needle 50.

As best illustrated in FIGS. 3 and 9, the rear housing piece 142 has a generally cylindrical portion 160 at the forward end of the rear housing. The cylindrical portion 160 is received in an annular flange 161 at the rear of the front housing piece 62. The cylindrical portion 160 has an aperture 163 through which the guide tube 78 passes. As best illustrated in FIGS. 3 and 4, the cylindrical portion 160 carries a retaining ring 164 in a groove for holding the cylindrical portion 160 within the flange 161 of the front housing piece 62. The ring 164 causes the rear housing pieces 140 and 142 to be biased forwardly with the cylindrical portion 160 until the rear housing pieces 140 and 142 engage the front housing pieces 62 and 64. This serves to hold together the rear housing 70 and front housing 60.

As best illustrated in FIG. 9, the annular portion of the front housing piece 62 includes a plurality of circumferential spaced bores 170. These bores 170 are adapted to receive an indexing pin 172 carried in a channel 174 of the rear housing piece 142. The indexing pin 172 is biased forwardly into one of the bores 170 by means of a compression spring 176 which is disposed within the bore 174 between the end of the bore and the indexing pin 172.

The indexing pin has an upwardly extending member or button 178 adapted to be engaged by the thumb of the surgeon operating the fastener applier device 20. As best illustrated in FIG. 1, the button 178 is adapted to reciprocate within a channel 182 defined in the mating housing pieces 140 and 142.

The front housing portion 60 and the rear housing portion 70 can be rotated relative to each other. Specifically, the front housing piece 62 (together with the front housing piece 64 connected to the piece 62) can be rotated together relative to the rear housing portion 70 about the cylindrical portion 160 when the indexing pin 172 is pulled rearwardly out of engagement with the bores 170. When the desired orientation of the needle 50, relative to the trigger 79, is obtained, the indexing pin 172 is released by the surgeon. The indexing pin 172 is then forced forwardly by the spring 176 against the front housing piece 62. An additional slight rotational movement of the front housing portion 60, in either direction of rotation, may be necessary to align one of the bores 170 with the indexing pin 172, whereupon the indexing pin 172 is driven further forwardly by the spring 176 into a bore 170 to thereby lock the front housing portion 60 relative to the rear housing portion 70.

THE HYDRAULIC ACTUATING MECHANISM

The rear housing portion 70 contains the novel actuating mechanism or means for reciprocating the flexible pusher member 74 between the retracted position and the extended position. The actuating mechanism is next described in detail with reference to FIGS. 10, 11, 12, and 13 which illustrate the interior structure of the rear housing portion 70 of the fastener applier device.

FIGS. 10 and 12 show the rear housing piece 142 viewed along its parting plane with certain interior components illustrated in cross section. For ease of illustration in FIGS. 10, 11, and 12, the front housing portion (portion 60 in FIG. 3) has not been shown and the indexing pin and its biasing spring (reference numerals 172 and 176, respectively, in FIG. 3) have likewise not been shown. Also, for convenience of illustration, some of the housing structure has been eliminated from FIG. 12.

The rear housing portion 70 contains a hydraulic actuating system module which includes two mating pieces, piece 180 and piece 182, that together define an inner housing for certain other components of the hydraulic system. Pieces 180 and 182 are secured together by suitable means (not illustrated) along a plane indicated by the line 183 in FIG. 11. The piece 180 is suitably mounted to the rear housing portion 70. Specifically, with reference to FIG. 10, the piece 180 is mounted to housing piece 142 by means of screws 185. Piece 182, which is secured to the piece 180, may be similarly mounted to the other rear housing piece 142 if desired.

The module piece 182 defines one-half of a first chamber 301 and one-half of a second chamber 302. The other module piece 180 defines the other halves of the first and second chambers 301 and 302, respectively. The chambers 301 and 302 are connected via a conduit 309 so that the interior volume of chamber 301 communicates with the interior volume of chamber 302.

The chambers 301 and 302 are generally cylindrical. The second chamber 302 is oriented with its longitudinal axis at an angle relative to the longitudinal axis of the first chamber 301. The first chamber 301 has a length greater than that of the second chamber 302. However, the diameter of the first chamber 301 is less than the diameter of the second chamber 302.

A first piston 321 is slidably disposed in the first chamber 301. The first piston 321 is provided with a pair of spaced-apart annular sealing rings or O-rings 323. The first piston 321 is adapted to be moved along chamber 301 between a first position illustrated in FIG. 10 and a second position illustrated in FIG. 12.

Extending from one end of the first piston 321 is a rod 311 as best illustrated in FIGS. 10, 12, and 13. A connecting bar 313 is secured at one end to the rod 311 and at the other end to the flexible pusher 74. A cavity 315 is defined by the module pieces 180 and 182 for receiving the bar 313. The cavity 315 communicates with the first chamber 301 (at the left-hand end of chamber 301 as viewed in FIGS. 10 and 12) and also along the bottom of the chamber 301 as viewed in FIG. 13.

The bar 313 has a downwardly depending portion 314 at its forward end to which is secured an end of a Hunter type constant force negator spring 324. The coiled portion of the spring 324 is received in a cavity 316 communicating with cavity 315. The spring 324 is restrained at the coiled end in the slot of a cross pin 317. The spring 324 functions as a first piston biasing means to bias the first piston 321 toward the second chamber 302.

The end of the guide tube 78 is received in the module pieces 180 and 182 as best illustrated in FIG. 10. The guide tube 78 projects forwardly beyond the module pieces 180 and 182 away from the cavity 315 and into the front housing portion 60 wherein the guide tube 78 is arranged to guide the flexible pusher 74 into the channel 72 as described above with reference to FIG. 3. In the rear housing portion 70, the flexible pusher 74 extends from the guide tube 78, through an aperture 189 in the module pieces 180 and 182, and into the cavity 315 and first chamber 301 where the pusher 74 is secured to the bar 313.

As best illustrated in FIG. 10, a second piston 322 is slidably disposed within the second chamber 302. The second piston 322 has a pair of spaced-apart annular flanges 333 for sealingly engaging the cylindrical sidewall of the second chamber 302.

A substantially incompressible fluid (not illustrated) is contained within the connected first and second chambers 301 and 302, respectively, between the first and second pistons 321 and 322, respectively. Preferably, the fluid is a sterile liquid, such as sterilized water. The fluid can be introduced into the chambers 301 and 302 by means of an aperture at the top of conduit 309 that is subsequently sealed with a plug 310 as best illustrated in FIG. 10.

Each piston 321 and 322 can be regarded as having a pressure bearing working surface that comprises the surface of the piston in contact with the fluid in the chambers. The working surface of each piston need not necessarily be perpendicular to the longitudinal axis of the chamber in which the piston is disposed, and hence, to the direction of movement of the piston. The amount of force exerted by the piston on the fluid, or by the fluid upon the piston, is proportional to the projection area of the pressure bearing working surface of the piston normal to the direction of the piston movement. Preferably, as in the embodiment illustrated in FIGS. 10-13, the projection area of the pressure bearing working surface of the first piston 321 normal to the direction of the first piston movement is less than the projection area of the pressure bearing working surface of the second piston 322 normal to the direction of the second piston movement.

Further, the volume of the second chamber 302 (as determined by the length of the stroke of the piston 322 within the second chamber 302) is equal to the volume of the first chamber 301 (as determined by the length of the stroke of the first piston 321 in the first chamber 301). Consequently, movement of the second piston 322 (by means described in detail hereinafter) toward the first piston 321 will cause the first piston 321 to move from the first position (FIG. 10) along the length of the first chamber 301 until the volume of fluid discharged from the second chamber 302 has been received in the first chamber 301. At this point the first piston 321 is at the second position illustrated in FIG. 12. Since the diameter of the first chamber 301 is less than the diameter of the second chamber 302 as described above, the stroke of the first piston 301 between the first and second positions is necessarily greater than the corresponding stroke of the second piston 322. In this manner, the movement of the connected pusher member 74 is amplified relative to the movement of the second piston 322.

The second piston 322 is moved in the chamber 302 by the trigger 79 in cooperation with a novel mechanism. The second piston 322 carries a rod or cam follower means 340 on a portion of the piston 322 that faces away from the piston pressure bearing working surface. The trigger 79 has an interior planar camming surface 345 defining a camming means that is engaged with the second piston cam follower means 340.

When it is desired to apply a fastener 30 with the device 20, the trigger or handle 79 is squeezed upwardly to a fully actuated position as illustrated in FIG. 12. This forces the second piston 322 along the second chamber 302 to force the hydraulic fluid into the first chamber 301. The first piston 321 is thus moved along the first chamber 301 (to the left as viewed in FIG. 7) and compresses spring 324. In this manner, the flexible pusher member 74 is moved through the housing of the device to eject a fastener 30 from the needle 50 as described above in detail with reference to FIGS. 1–9.

Preferably, as best illustrated in FIGS. 10, 11, and 12, a handle biasing means or spring 360 is provided to help pivot the handle 79 outwardly to an unactuated or released position. The spring 360 is wound around the handle of pivot shaft 150 and has a first end or loop 362 engaged with the hydraulic system module pieces 180 and 182 and has a second end or loop 364 engaged with the trigger 79.

Of course, depending upon the strength of the spring 324 connected to the first piston 321, the spring 360 may not be required. If the spring 324 has a sufficiently high force, release of the trigger 79 by the surgeon will permit the spring 324 to drive the piston 321 to the end of the first chamber 301. This will cause the second piston 322 to be driven to the end of the second chamber 302 and to thereby return the trigger 79 to the fully released position.

When the trigger 79 is released by the surgeon operating the fastener applier device 20, the first piston 321 returns to the beginning of its stroke and hence, the connected flexible pusher member 74 is returned to the retracted position wherein the leading end of the pusher member 74 is located behind the dispensing region adjacent the magazine 100 to permit the next fastener 30 to be moved into the dispensing region in alignment with the needle 50 as described above with reference to FIGS. 1–9.

Instead of providing sliding pistons with seals as illustrated for pistons 321 and 322, it may be desirable to provide chambers similar to chambers 301 and 302, but modified to include reciprocative sealed bellows structures at each end to function as pistons. This would provide a leak-tight design.

Although the hydraulic actuating mechanism described above is particularly useful when incorporated in a fastener applier device 20 for applying fasteners 30, it is to be realized that the hydraulic actuating mechanism may be incorporated in other instruments. Such other instruments may have flexible or rigid pusher members for pushing a foreign body, other than a fastener, into tissue.

Also, such other instruments may instead incorporate one or more other types of movable operating elements or members. Such other instruments may include instruments for applying ligating clips to blood vessels, bone crushing instruments, pin cutting instruments, and instruments for applying staples to tissue.

Further, in accordance with the teachings of the present invention, the diameter of the first piston 321 could be greater than the diameter of the second piston 322 so that the force of the operating member could be amplified relative to the force applied at the handle of the device.

From the foregoing, it will be observed that numerous variations and modifications may be effected without departing from the true spirit and scope of the novel concept of the invention. It is to be understood that no limitation with respect to the specific apparatus and method illustrated herein is intended or should be inferred. It is, of course, intended to cover by the appended claims all such modifications as fall within the scope of the claims.

We claim:

1. In a hand-operated surgical instrument for implanting a fastener in tissue to close a wound in the tissue, said instrument having at least one movable operating member for implanting the fastener in tissue, said operating member being disposed remote from or extending from a movable handle means for actuating said member, the improvement characterized in that a hydraulic actuating means is operably connected between said handle means and said operating member for effecting the movement of said operating member to implant said fastener when said handle means is moved relative to said instrument, said actuating means comprising:

first and second connected chambers rigidly disposed in said instrument, each said chamber having a generally cylindrical configuration and said second chamber being oriented with its longitudinal axis at an angle relative to the longitudinal axis of said first chamber;

first and second pistons slidably disposed in said first and second chambers respectively;

a substantially incompressible fluid occupying the volume within said connected first and second chambers between said first and second pistons;

means connecting said operating member with said first piston;

caming means associated with said handle means and cam follower means connected with said second piston for engaging said camming means and being moved by said handle means to force said second piston along said second chamber thereby forcing said fluid from said second chamber into said first chamber to move said first piston from a first piston to a second piston to effect said movement of the connected operating member; and first piston biasing means for biasing said first piston from said second position to said first position.

2. The improvement in accordance with claim 1 in which the interior volumes of said first and second chambers are connected with a conduit.

* * * * *